United States Patent
Jeong et al.

(10) Patent No.: US 10,010,310 B2
(45) Date of Patent: Jul. 3, 2018

(54) MINIMALLY INVASIVE SURGICAL INSTRUMENT

(76) Inventors: Chang Wook Jeong, Seoul (KR); Hyung Tae Kim, Incheon (KR)

(*) Notice: Subject to any disclaimer, the term of this patent is extended or adjusted under 35 U.S.C. 154(b) by 688 days.

(21) Appl. No.: 13/988,509

(22) PCT Filed: Nov. 18, 2011

(86) PCT No.: PCT/KR2011/008851
§ 371 (c)(1),
(2), (4) Date: Oct. 10, 2014

(87) PCT Pub. No.: WO2012/067468
PCT Pub. Date: May 24, 2012

(65) Prior Publication Data
US 2015/0032125 A1    Jan. 29, 2015

(30) Foreign Application Priority Data
Nov. 18, 2010    (KR) ........................ 10-2010-0115152

(51) Int. Cl.
*A61B 17/00*    (2006.01)
*A61B 17/29*    (2006.01)
*A61B 34/00*    (2016.01)

(52) U.S. Cl.
CPC ........ *A61B 17/00234* (2013.01); *A61B 17/29* (2013.01); *A61B 34/70* (2016.02);
(Continued)

(58) Field of Classification Search
CPC ............. A61B 17/00234; A61B 17/29; A61B 2017/00238; A61B 2017/003;
(Continued)

(56) References Cited

U.S. PATENT DOCUMENTS

| 6,676,684 B1 * | 1/2004 | Morley ................. A61B 34/71 606/205 |
| 2002/0040217 A1 | 4/2002 | Jinno |

(Continued)

FOREIGN PATENT DOCUMENTS

EP    01-886630 A2    2/2008

OTHER PUBLICATIONS

International Search Report for the International Application No. PCT/KR2011/008851, Korean Intellectual Property Office, dated Jun. 19, 2012.

*Primary Examiner* — Jocelin Tanner
(74) *Attorney, Agent, or Firm* — Dinsmore & Shohl LLP (57) ABSTRACT

A minimally invasive surgical instrument is provided, comprising a shaft and an end effector connected to the shaft, wherein the end effector operates in the pitch or yaw direction against the shaft when a first wire and a second wire conveyed through the shaft operate cooperatively according to a first aspect; and the end effector operates in the roll direction against the shaft when the first wire and the second wire operate cooperatively according to a second aspect, wherein the first wire and the second wire operate in the same direction when the cooperative operation is according to one aspect of the first aspect and the second aspect; and the first wire and the second wire operate in the opposite directions when the cooperative operation is according to the other aspect of the first aspect and the second aspect.

19 Claims, 6 Drawing Sheets

(52) U.S. Cl.
CPC .... *A61B 34/71* (2016.02); *A61B 2017/00367* (2013.01); *A61B 2017/2902* (2013.01); *A61B 2017/2927* (2013.01); *A61B 2017/2929* (2013.01); *A61B 2017/2946* (2013.01)

(58) Field of Classification Search
CPC .......... A61B 2017/00318; A61B 2017/00323; A61B 2017/00327; A61B 2017/00331; A61B 2017/00349; A61B 2017/00367; A61B 2017/00371; A61B 2017/00389; A61B 2017/00393; A61B 2017/00398; A61B 2017/00411; A61B 2017/2902; A61B 2017/2903; A61B 2017/2913; A61B 2017/2927; A61B 2017/2929; A61B 2017/2932; A61B 2017/2946; A61B 34/70; A61B 34/71; A61B 34/74; A61B 1/005; A61B 1/0052; A61B 1/0057; A61B 1/008; A61B 1/00133
See application file for complete search history.

(56) References Cited

U.S. PATENT DOCUMENTS

| | | | |
|---|---|---|---|
| 2003/0100892 A1* | 5/2003 | Morley | A61B 17/062 606/1 |
| 2006/0079889 A1 | 4/2006 | Scott | |
| 2006/0190034 A1* | 8/2006 | Nishizawa | A61B 17/29 606/205 |
| 2006/0219065 A1* | 10/2006 | Jinno | A61B 34/71 81/383 |
| 2010/0004509 A1 | 1/2010 | Naito | |
| 2010/0016853 A1* | 1/2010 | Burbank | A61B 18/1445 606/48 |

* cited by examiner

MINIMALLY INVASIVE SURGICAL INSTRUMENT

FIELD OF THE INVENTION

This invention relates to a convenient, minimally invasive surgical instrument, and more specifically to a minimally invasive surgical instrument to allow a user to operate an end effector by controlling a handling unit or the like to perform a minimally invasive surgery in a sophisticated and convenient manner.

BACKGROUND

Minimally invasive surgery is a surgical approach that involves the use of instruments inserted through several tiny incision openings to perform a surgery causing minimal tissue trauma in human or animal bodies.

The minimally invasive surgery relatively reduces changes in metabolism of a patient in the period of post-surgical care, so it facilitates rapid recovery of the patient. Therefore, the minimally invasive surgery shortens the length of hospitalization of the patient after the surgery and allows the patient to return to normal physical activities in a short period of time. In addition, the minimally invasive surgery causes less pain and leaves fewer scars on the patient's body after the surgery.

One of the general forms of the minimally invasive surgery is endoscopy. Among the others, a laparoscopy that involves minimally invasive inspection and operation inside abdominal cavity is known as the most general form of endoscopy. To operate a standard laparoscopic surgery, the abdomen of the patient is insufflated with gas and at least one small incision is formed to provide an entrance for laparoscopic surgical instruments, through which a trocar is inserted. When performing the surgery, it is general that a user puts the laparoscopic surgical instruments into a surgical site or the like through the trocar, and manipulates the instruments from the outside of abdominal cavity. In general, the laparoscopic surgical instruments include a laparoscope (for observation of a surgical site) and other working tools. Herein, the working tools are similar to the conventional tools used for small incision surgery, except that the end effector or working end of each tool is separated from its handle or the like by a shaft. For instance, the working tools may include a clamp, a grasper, scissors, a stapler, a needle holder, and so forth. Meanwhile, the user monitors the procedure of the surgery through a monitor that displays the images of the surgical site which are taken by the laparoscope. The endoscopic approaches similar to the above are broadly used in retroperitoneoscopy, pelviscopy, arthroscopy, cisternoscopy, sinuscopy, hysteroscopy, nephroscopy, cystoscopy, urethroscopy, pyeloscopy, and so on.

The inventor(s) has developed various minimally invasive surgical instruments useful for the above-mentioned minimally invasive surgeries and has already disclosed the features of the structures and effects of the same in Korean Patent Application Nos. 2008-51248, 2008-61894, 2008-79126 and 2008-90560, the contents of which are incorporated herein by reference in its entirety. Additionally, the inventor(s) will provide a minimally invasive surgical instrument with improved functionality, which is more advantageous for users and patients.

SUMMARY OF THE INVENTION

One object of the present invention is to provide a minimally invasive surgical instrument to allow a user to easily fix the joint motion states of its end effector.

Another object of this invention is to provide a minimally invasive surgical instrument to allow a user to easily conduct the rolling of its end effector.

Yet another object this invention is to provide a minimally invasive surgical instrument to allow a user to conduct the rolling of its end effector while the joint motion states of the end effector are fixed and maintained.

Still another object of this invention is to provide a minimally invasive surgical instrument that may be advantageously used in combination with a motor-based system.

According to one aspect of the invention to achieve the objects as described above, there is provided a minimally invasive surgical instrument comprising a shaft and an end effector connected to the shaft, wherein the end effector operates in the pitch or yaw direction against the shaft when a first wire and a second wire operate cooperatively according to a first aspect conveyed through the shaft; and the end effector operates in the roll direction against the shaft when the first wire and the second wire operate cooperatively according to a second aspect, wherein the first wire and the second wire operate in the same direction when the cooperative operation is according to one aspect of the first aspect and the second aspect; and the first wire and the second wire operate in the opposite directions when the cooperative operation is according to the other aspect of the first aspect and the second aspect.

In addition, there may be provided other ways to implement this invention.

According to the invention, there is provided a minimally invasive surgical instrument to allow a user to easily fix the joint motion states of its end effector.

According to the invention, there is provided a minimally invasive surgical instrument to allow a user to easily conduct the rolling of its end effector.

According to the invention, there is provided a minimally invasive surgical instrument to allow a user to conduct the rolling of its end effector while the joint motion states of the end effector are fixed and maintained.

According to the invention, there is provided a minimally invasive surgical instrument that maybe advantageously used in combination with a motor-based system.

DETAILED DESCRIPTION OF THE PREFERRED EMBODIMENTS

In the following detailed description of the invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures, or characteristics described herein may be implemented as modified from one embodiment to another embodiment without departing from the spirit and the scope of the invention. Furthermore, it shall be understood that the locations or arrangements of individual elements within each embodiment may be also modified without departing from the spirit and the scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, preferred embodiments of the present invention will be described in detail with reference to the accompanying drawings to enable those skilled in the art to easily implement the invention.

First Embodiment

Figure 1:
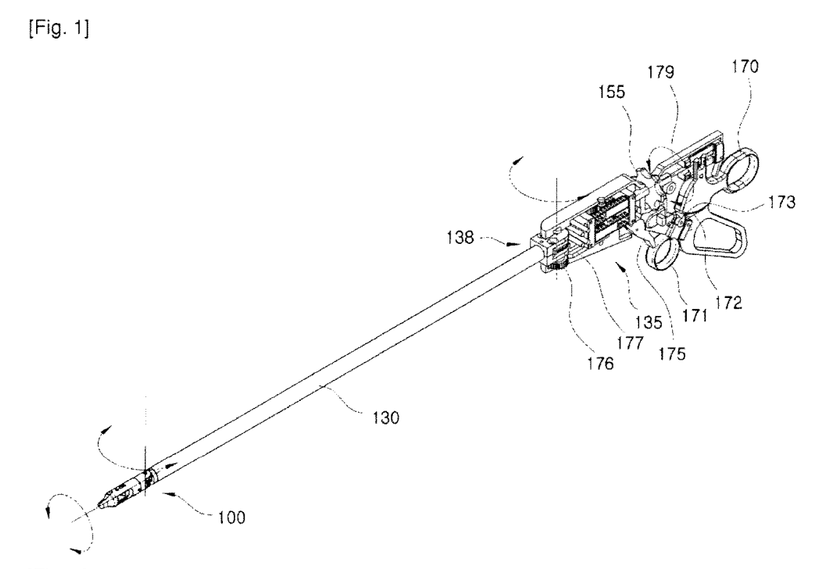
FIG. 1 shows a perspective view of the minimally invasive surgical instrument according to a first embodiment of the invention.
Figure 2:
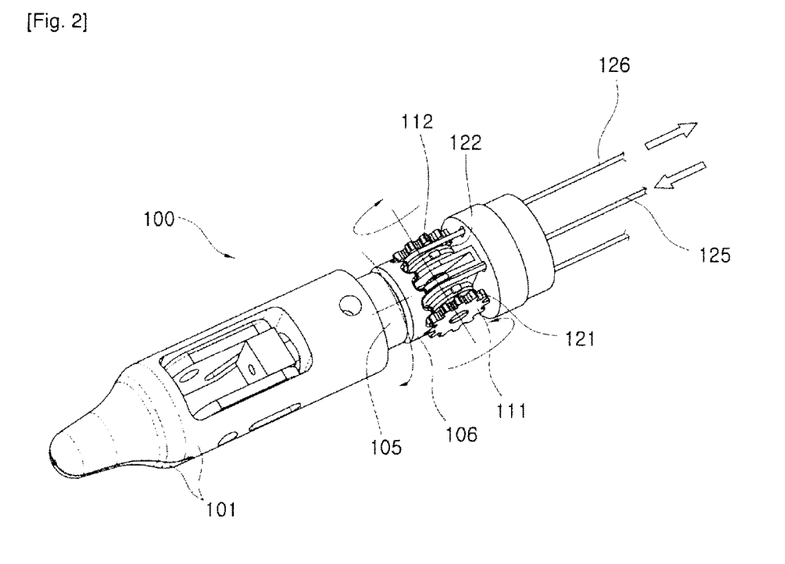
FIG. 2 shows an enlarged view of the end effector 100 shown in FIG. 1.

FIG. 1 shows a perspective view of the minimally invasive surgical instrument according to a first embodiment of the invention. Further, FIG. 2 shows an enlarged view of the end effector 100 shown in FIG. 1.

First, reference will be made to FIG. 1. The minimally invasive surgical instrument according to one embodiment of the invention may comprise an end effector 100 to perform surgery by acting as a surgical instrument or using other surgical instruments; a shaft 130 connecting the end effector 100 and a handling unit 135, wherein the end effector 100 (or the part thereof) is disposed on one end such that it may operate in the yaw or roll direction and the handling unit 135 is disposed on the other end; and the handling unit 135 to control the end effector 100 to operate in the yaw or roll direction (A part of the end effector 100 may be open or closed by way of the control of the handling unit 135). Herein, the shaft 130 is a component elongated to insert surgical instruments or the like into a surgical site through a trocar, and through the shaft 130, the wires may be disposed to operate the end effector 100 according to the control of the handling unit 135. The wires may be disposed such that they do not get tangled with each other inside of the shaft 130.

Meanwhile, other components shown in FIG. 1 will be discussed later with reference to other drawings and descriptions thereof as mentioned below. Next, reference will be made to FIG. 2.

The end effector 100 may comprise pincers 101 (also referred to as "holders") to hold surgical instruments. The pincers 101 can be opened or closed by an opening/closing wire (not shown). The opening/closing wire may transmit the force for opening or closing the pincers 101 from the handling unit 135 to the pincers 101 since one end of the wire is connected to the pincers 101 and the other end is connected to the handling unit 135. An elastic component such as a spring (not shown) may be used together to control either of the opening or closing of the pincers 101.

Meanwhile, the end effector 100 may comprise a connecting component 105 for connecting and fixing the pincers 101 or the like to a roll gear 106 (to be described below) to enable the pincers 101 or the like to operate in the roll direction; the roll gear 106 to operate the pincers 101 or the like and the connecting component 105 in the roll direction; and a first pinion 111 and a second pinion 112 geared to the roll gear 106 on the opposite side of the connecting component 105 to rotate the roll gear 106. A first pulley 121 and a second pulley 122 may be combined to the first pinion 111 and the second pinion 112, respectively.

More specifically, the first pinion 111 and the second pinion 112 may rotate in the same direction or in the opposite directions by way of the actions of the first wire 125 and the second wire 126 wound around the first pulley 121 and the second pulley 122, respectively. In other words, if the first wire 125 and the second wire 126, respectively, rotate the first pulley 121 and the second pulley 122 in the opposite directions to each other, and further rotate the first pinion 111 and the second pinion 112 in the opposite directions to each other, then the roll gear 106 rotates so that the pincers 101 or the like may operate in the roll direction. However, if the first wire 125 and the second wire 126, respectively, rotate the first pinion 111 and the second pinion 112 in the same direction, then the roll gear 106 does not rotate itself but instead only acts as a component transmitting the force to operate the pincers 101 or the like in the yaw direction.

It will be discussed later how to control the first wire 125 and the second wire 126 to act in the above-mentioned manner.

Figure 3:
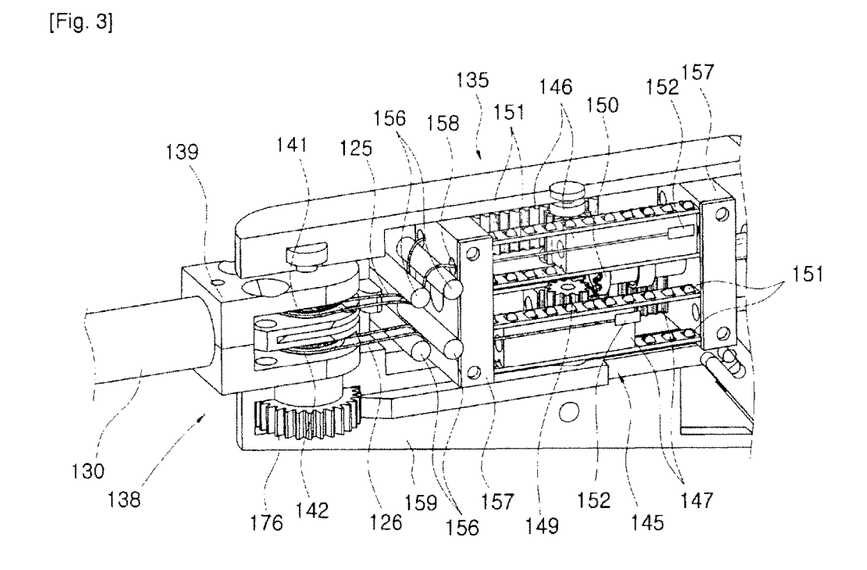
FIG. 3 shows an enlarged view of the handling unit 135 shown in FIG. 1.
Figure 4:
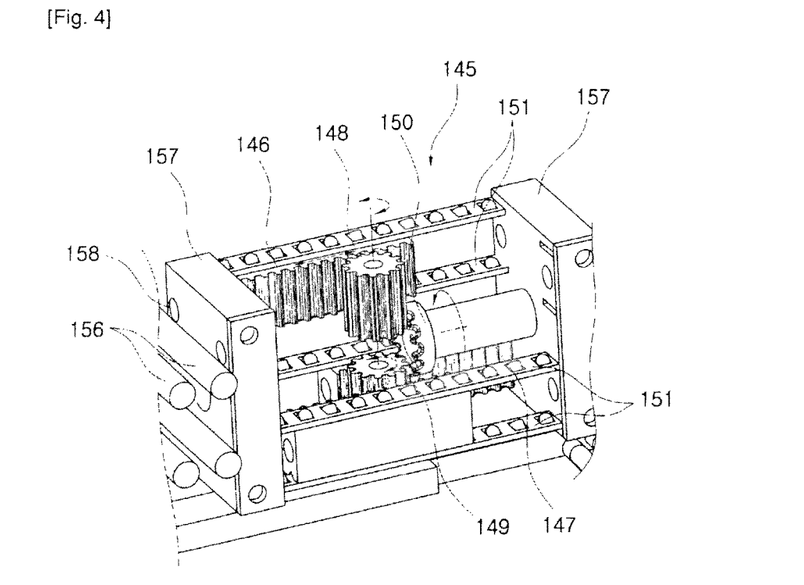
FIG. 4 shows an enlarged view of the roll control unit 145 shown in FIG. 3.

FIG. 3 shows an enlarged view of the handling unit 135 shown in FIG. 1. Further, FIG. 4 shows an enlarged view of the roll control unit 145 shown in FIG. 3.

First, reference will be made to FIG. 3.

The handling unit 135 may comprise a yaw control unit 138 connected and fixed to one end of the shaft 130 to control the end effector 100 to operate in the yaw direction; a roll control unit 145 to control the end effector 100 to operate in the roll direction; and a main control unit 159 comprising and supporting the yaw control unit 138 and the roll control unit 145.

The yaw control unit 138 may comprise a main yaw control unit 139 as well as a third pulley 141 and a fourth pulley 142. The main yaw control unit 139 may be connected and fixed to one end of the shaft 130. A rotation axis is inserted in the main yaw control unit 139 to rotate the third pulley 141 and the fourth pulley 142 together with the part of the handling unit 135 except the main yaw control unit 139 (i.e., to act as a fixed axis with respect to the third pulley 141 and the fourth pulley 142 as well as the part of the handling unit 135 except the main yaw control unit 139), and the rotation axis may rotate together with the above components against the main yaw control unit 139. Furthermore, since the first wire 125 and the second wire 126 are wound around the third pulley 141 and the fourth pulley 142, respectively, controlling the main control unit 159 to rotate the third pulley 141 and the fourth pulley 142 in the same direction may cause the operation of the end effector 100 in the yaw direction as described above.

Hereinafter, further reference will be made to FIG. 4.

Meanwhile, the roll control unit 145 may comprise a pair of upper rack gears 146 connected with the first wire 125 to operate in the longitudinal direction; a pair of lower rack gears 147 connected with the second wire 126 to operate in the longitudinal direction; an upper pinion 148 geared between the pair of upper rack gears 146; a lower pinion 149 geared between the pair of lower rack gears 147; and a roll control gear 150 commonly geared to the upper pinion 148 and the lower pinion 149.

The pair of upper rack gears 146 herein is a pair of rack gears geared to both sides of the upper pinion 148 to operate in the opposite directions to each other according to the operation of the upper pinion 148. Further, the pair of lower rack gears 147 is also a pair of rack gears geared to both sides of the lower pinion 149 to operate in the same way. The upper rack gears 146 and the lower rack gears 147 may operate along the rail 151 (Note that the part of the rail 151 for the upper rack gear 146 is not illustrated in FIG. 4 for easier viewing of other components). On the other hand, as shown in FIG. 3, each end of the upper rack gear 146 and the lower rack gear 147 is provided with a control screw 152, to which the first wire 125 or the second wire 126 may be connected. The control screw 152 may function to control the tension of the wires (125, 126).

Meanwhile, the upper pinion 148 and the lower pinion 149 may rotate around an axis disposed in the main control unit 159 (now shown). The roll control gear 150 may be connected to the roll sprocket 155 shown in FIG. 1 (which may be combined to the main control unit 159 to rotate against it) to rotate as the user rotates the roll sprocket 155, such that the upper pinion 148 and the lower pinion 149 may rotate in the opposite directions to each other. Such rotations of the upper pinion 148 and the lower pinion 149 may cause the actions of the pair of the upper rack gears 146 and the pair of the lower rack gears 147 to allow the first wire 125 and the second wire 126 to operate in the opposite directions to each other, which may eventually cause the operation of the end effector 100 in the roll direction as described above.

Furthermore, two pairs of support bars 156, which support the first wire 125 and the second wire 126 between the yaw control unit 138 and the roll control unit 145, respectively, may be further disposed in the main control unit 159. A guide block 157 formed with guide holes 158 to guide the conveyance of the first wire 125 and the second wire 126 toward the roll control unit 145 may be disposed between the support bars 156 and the roll control unit 145. The guide block 157 may be combined to the end of the rail 151.

Meanwhile, other components shown in FIG. 3 will be discussed later with reference to other drawings and descriptions thereof as mentioned below.

Second Embodiment

Figure 5:
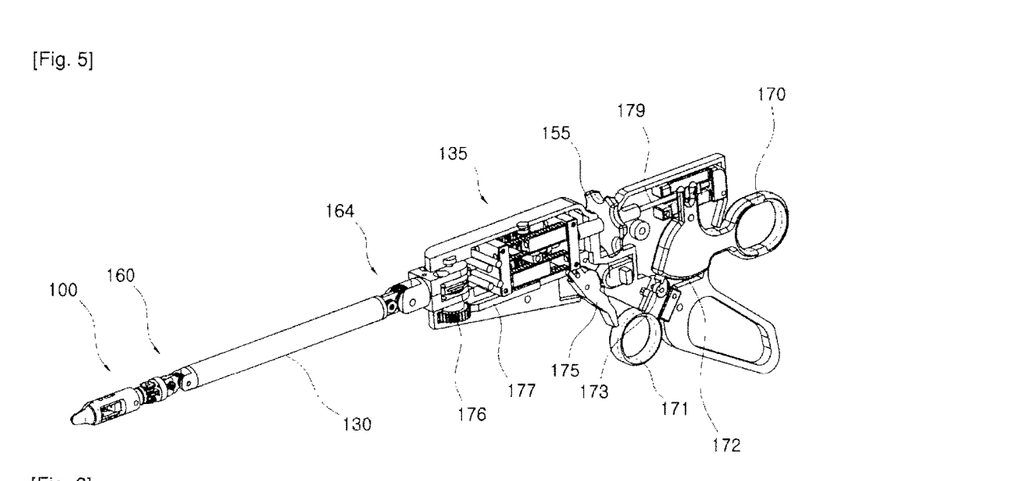
FIG. 5 shows a perspective view of the minimally invasive surgical instrument according to a second embodiment of the invention.

FIG. 5 shows a perspective view of the minimally invasive surgical instrument according to a second embodiment of the invention. Further, FIG. 6 shows an enlarged view of the end effector 100 and the pitch operating unit 160 shown in FIG. 5.

Figure 6:
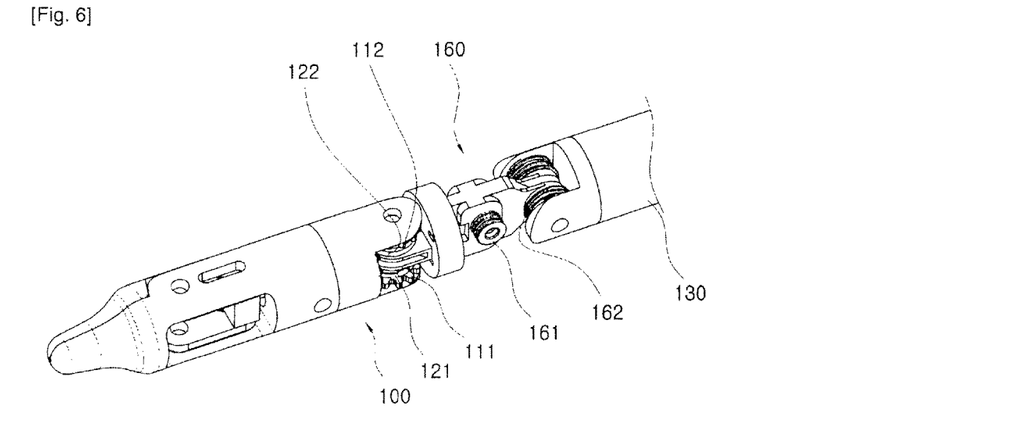
FIG. 6 shows an enlarged view of the end effector 100 and the pitch operating unit 160 shown in FIG. 5.

With reference to FIG. 5 and FIG. 6, it may be seen that the minimally invasive surgical instrument according to the second embodiment of the invention comprises the similar components for operating the end effector 100 in the yaw or roll direction as described in conjunction with the first embodiment. Thus, the components unique to the second embodiment will be mainly described below.

As shown in FIG. 5, the minimally invasive surgical instrument according to the second embodiment of the invention may further comprise a pitch operating unit 160 and a pitch control unit 164 disposed at both ends of the shaft 130 to operate the end effector 100 in the pitch direction. Specifically, the pitch operating unit 160 may be disposed between the end effector 100 and the shaft 130, and the pitch control unit 164 may be disposed between the shaft 130 and the handling unit 135.

As shown in FIG. 6, the pitch operating unit 160 may be disposed between the end effector 100 and the shaft 130 to operate the end effector 100 in the pitch direction. Herein, there may be further provided a plurality of pulleys (161, 162) as illustrated. The actions of such pulleys will be described below.

Meanwhile, other components shown in FIG. 5 will be discussed later with reference to other drawings and descriptions thereof as mentioned below.

Figure 7:
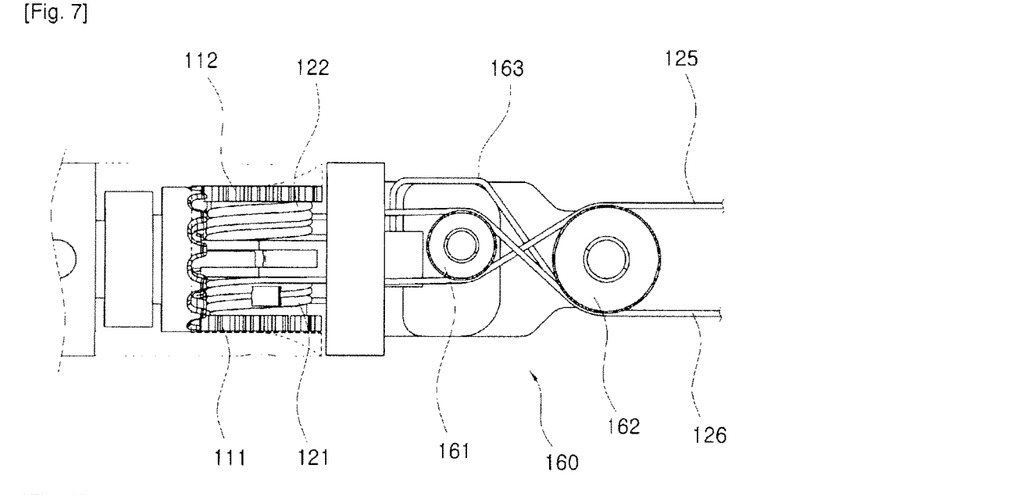
FIG. 7 shows a lateral view of the pitch operating unit 160 shown in FIG. 6.
Figure 8:
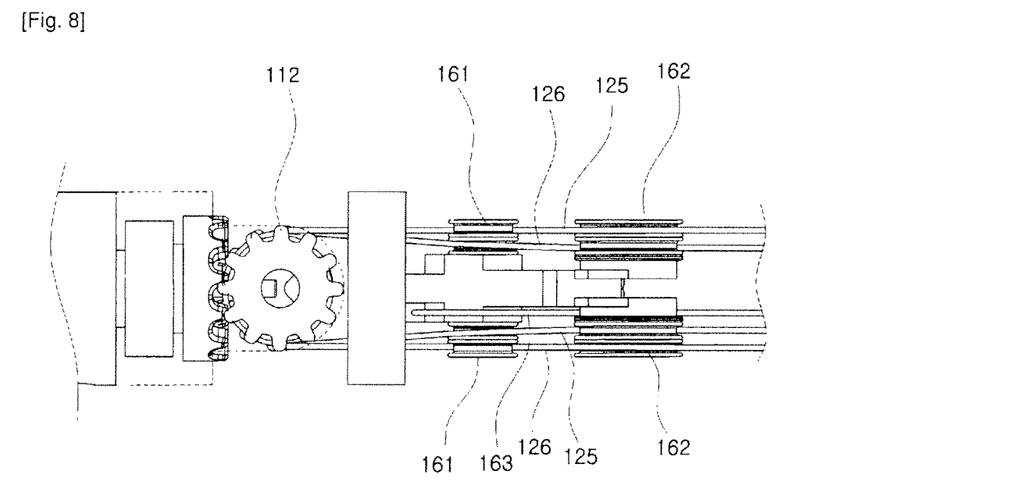
FIG. 8 shows a top view of the same.

FIG. 7 shows a lateral view of the pitch operating unit 160 shown in FIG. 6, and FIG. 8 shows a top view of the same.

With reference to FIGS. 6 to 8, the first wire 125 and the second wire 126 may pass through the pitch operating unit 160, and first pitch pulleys 161 and second pitch pulleys 162, which may support the wires, may be provided in the pitch operating unit 160. The (virtual) rotation planes of the pitch pulleys (161, 162) may be substantially orthogonal to the rotation planes of the first pulley 121 and the second pulley 122.

The first wire 125 from the handling unit 135 and the shaft 130 may be wound around the first pulley 121 after passing the upper parts of the second pitch pulleys 162 and then the lower parts of the first pitch pulleys 161, as shown in FIG. 7. Thus, seen from the lateral side of the pitch operating unit 160, the part of the first wire 125 passing the first pitch pulleys 161 and the second pitch pulleys 162 may form an 'X' shape together with the part of the second wire 126 passing and being wound as illustrated, i.e., in the same way as above (Note that such arrangement may be advantageous in maintaining and supporting the tension of the first wire 125 and the second wire 126).

Meanwhile, the first wire 125 may be wound around the first pulley 121 after passing the first and third ones of the plurality of second pitch pulleys 162 and then passing the first and third ones of the plurality of first pitch pulleys 161, as shown in FIG. 8. Further, the second wire 126 may be wound around the second pulley 122 after passing the second and fourth ones of the plurality of second pitch pulleys 162 and then passing the second and fourth ones of the plurality of first pitch pulleys 161, as shown in FIG. 8. Therefore, the first wire 125 and the second wire 126 may be disposed without getting tangled with each other in the pitch operating unit 160, as shown in FIG. 8.

Meanwhile, as shown in FIG. 7, a first pitch wire 163 may be connected and fixed to the side of the pitch operating unit 160 facing the end effector 100 to operate the end effector 100 in the pitch direction. Further, a second pitch wire (not shown) may be connected and fixed to the invisible side of the same part in the same way as the first pitch wire 163 (Note that it is desirable to connect and fix the second pitch wire so that the direction in which the end effector 100 is operated by the second pitch wire (e.g., counterclockwise in FIG. 7) is opposite to the direction in which the end effector 100 is operated by the first pitch wire 163 (e.g., clockwise in FIG. 7)). The second pitch pulleys 162 for the operation of the end effector 100 in the pitch direction may be fixed pulleys (i.e. pulleys fixed on their axes).

Figure 9:
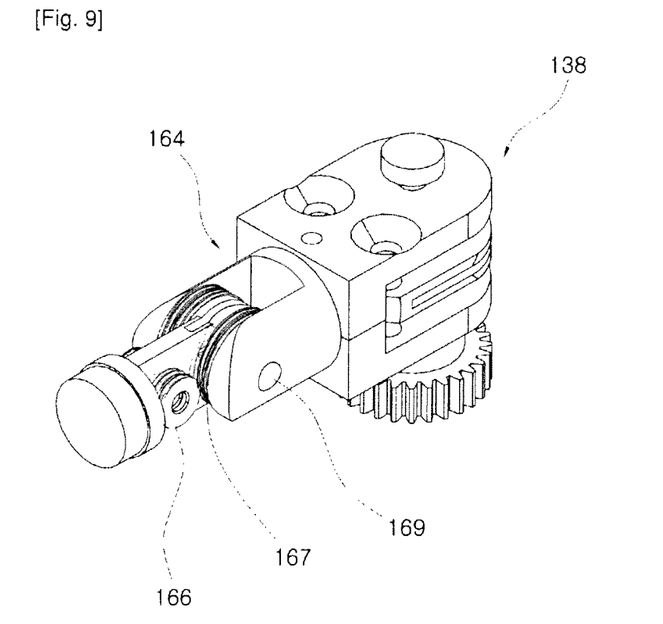
FIG. 9 shows a perspective view of the pitch control unit 164 and the yaw control unit 138 shown in FIG. 5.
Figure 10:
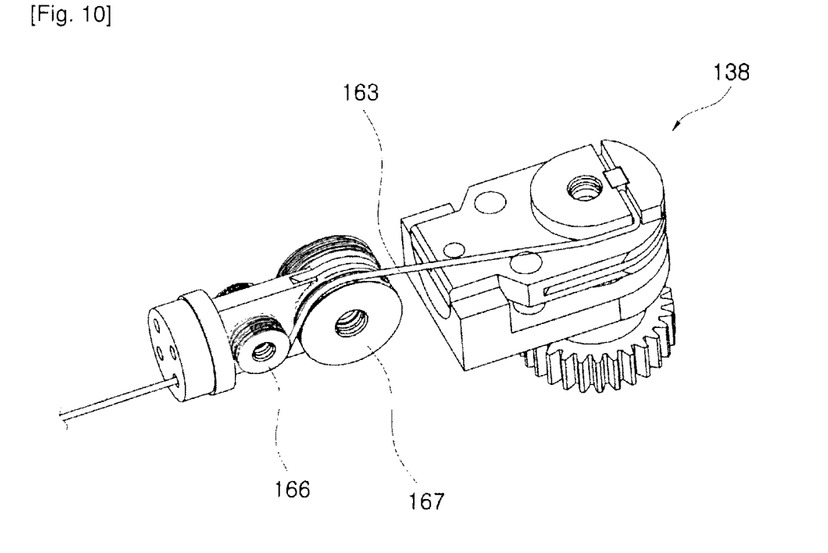
FIG. 10 shows an exploded perspective view of some components of the same.

FIG. 9 shows a perspective view of the pitch control unit 164 and the yaw control unit 138 shown in FIG. 5, and FIG. 10 shows an exploded perspective view of some components of the same.

Reference will now be made to FIGS. 9 and 10.

As shown in FIG. 10, one end of the first pitch wire 163, the other end of which is connected and fixed to the pitch operating unit 160 as described above, may be connected and fixed to the yaw control unit 138 through the shaft 130 and the pitch control unit 164. In this connection, the pitch control unit 164 may be provided in combination with the yaw control unit 138 as shown in FIG. 9.

More specifically, the first pitch wire 163 from the shaft 130 may be connected and fixed to one part of the yaw control unit 138 (e.g., the part as shown in FIG. 10) after passing third pitch pulleys 166 and fourth pitch pulleys 167, which are included in the pitch control unit 164. Thus, when the user controls the handling unit 135 down in the pitch direction (i.e., clockwise in FIGS. 9 and 10), the first pitch wire 163 is pulled to cause the end effector 100 to operate in the pitch direction as described above. The second pitch wire may be also connected and fixed in the same way as the first pitch wire 163 (Accordingly, when the user controls the handling unit 135 up in the pitch direction (i.e., counterclockwise in FIGS. 9 and 10), the second pitch wire is pulled to cause the end effector 100 to operate in the pitch direction as described above). Herein, the third pitch pulleys 166 may be rotating pulleys to facilitate the conveyance of the first pitch wire 163 and the second pitch wire, and the fourth pitch pulleys 167 may be fixed pulleys that are substantially fixed while the handling unit 135 operates in the pitch direction around a rotation axis (not shown) which may be inserted to the axial hole 169.

Although the present invention has been illustrated in connection with the second embodiment of the invention, it is apparent that a person of ordinary skill in the art may modify the second embodiment to operate the end effector 100 in the pitch direction by the action of the roll gear 106 and/or in the yaw direction by the action of another yaw operating unit (not shown).

Third Embodiment

Hereinafter, embodiments of the handling unit 135 that may be employed in the minimally invasive surgical instrument according to the first or second embodiment of the invention will be further discussed.

Reference will be made again to FIGS. 1 and 5. First, the main control unit 159 of the handling unit 135 may be provided with an opening/closing handle 170 to open and/or close the pincers 101 of the end effector 100. Thus, when the user pulls down the opening/closing handle 170 (i.e., rotates the opening/closing handle 170 clockwise), the opening/closing wire (connected from the opening/closing handle 170 to the pincers 101 through a connecting tube 179, the shaft 130, and the like) may be pulled to close the pincers 101 to hold surgical instruments. On the other hand, when the user releases up the opening/closing handle 170 (i.e., rotates the opening/closing handle 170 counterclockwise), the opening/closing wire may get slack to open the pincers 101. Meanwhile, the main control unit 159 may further comprise a fixing handle 171 to fix the position of the opening/closing handle 170 so that the opening/closing handle 170 may be fixed to maintain the open and/or closed states of the pincers 101 (particularly to maintain the pincers 101 to hold the surgical instruments). The fixing handle 171 may comprise another component 173 to fix a fixing gear 172 linked with the opening/closing handle 170 (e.g., a component 173 to mesh with the cogs of the fixing gear 172 to fix the fixing gear 172). Meanwhile, the fixing handle 171 may be disposed as shown in the drawings such that the user may easily grab the fixing handle 171 together with the opening/closing handle 170.

It is apparent that a person of ordinary skill in the art may modify the configurations described above in various ways, such as modifying the pincers 101 to be opened instead of being closed when the opening/closing handle 170 is pulled down.

Figure 11:
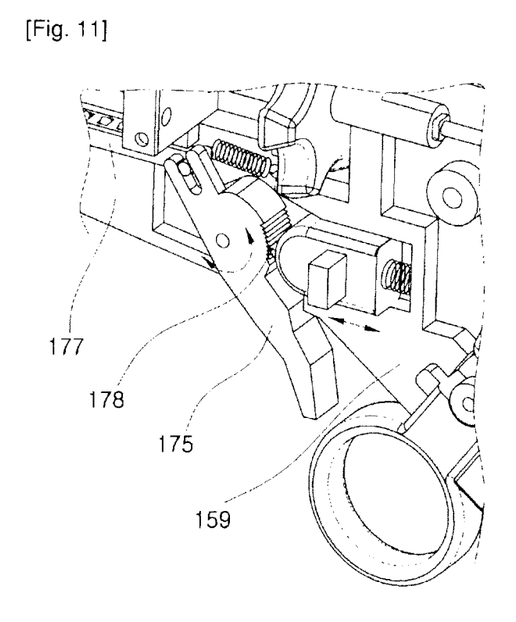
FIG. 11 shows an enlarged view illustrating how the yaw-direction operating states of the end effector 100 are fixed according to a third embodiment of the invention.

Next, further reference will be made to FIG. 11. FIG. 11 shows an enlarged view illustrating how the yaw-direction operating states of the end effector 100 are fixed according to a third embodiment of the invention. As shown in FIGS. 1 and 5, a fixing gear 176 may be disposed under the yaw control unit 138 such that it may be combined to and rotate together with the above rotation axis. As shown in FIG. 11, a latch trigger 175 may be disposed in the main control unit 159 to fix the rotation of the fixing gear 176. The latch trigger 175 may be connected to a fixing component 177, one end of which may mesh with the cogs of the fixing gear 176 to fix the fixing gear 176. The fixing component 177 may be disposed in the main control unit 159 to operate in the longitudinal direction as the user controls the latch trigger 175. The latch trigger 175 may be fixed by another hook 178 comprising an elastic body such as a spring component.

Meanwhile, although not explicitly described, some arrangements to fix the pitch-direction operating states of the end effector 100 (e.g., those including a certain type of fixing gear (not shown) combined to the rotation axis that may be inserted to the axial hole 169 as well as a component to fix the same (not shown)) may be further employed.

Fourth Embodiment

According to the fourth embodiment of this invention, at least a part of the handling unit 135 of the minimally invasive surgical instrument may be modified or changed to some components suitable for being driven by a motor-based system such as a surgical robot (not shown), so that the minimally invasive surgical instrument may be controlled by an automatic (or semi-automatic) control system, rather than being manually controlled by the user.

For example, an electric motor included in a surgical robot (not shown) may operate the end effector 100 in the pitch direction by directly pulling the first pitch wire 163 and/or the second pitch wire. Obviously, the electric motor may operate the end effector 100 in the pitch direction by directly controlling the modified handling unit 135 in the pitch direction.

For another example, an electric motor may operate the end effector 100 in the yaw or roll direction by directly pushing and pulling the first wire 125 and/or the second wire 126. Obviously, the electric motor may operate the end effector 100 in the yaw or roll direction by directly controlling the modified handling unit 135 in the yaw direction (alternatively, directly rotating the third pulley 141 and the fourth pulley 142 in the same direction) or directly rotating the roll sprocket 155 (alternatively, directly rotating the roll control gear 150).

For yet another example, an electric motor may control either of the opening or closing of the pincers 101 by directly pulling the opening/closing wire.

For still another example, a system may fix the joint motion states or the opening/closing states of the end effector 100 by directly controlling the drive of an electric motor.

Applications

A user may insert the end effector 100 of the minimally invasive surgical instrument according to the present invention in the vicinity of a surgical site, and then control the handling unit 135 to operate the end effector 100 in the pitch direction and/or the yaw direction (i.e., joint motion). After the desired joint motion of the end effector 100, the user may fix the states. Then the user may rotate the roll sprocket 155 in the desired direction so that the end effector 100 may operate in the roll direction with the above states maintained. Such operation of the end effector 100 may be particularly advantageous for sutures using round needles (not shown).

Although the present invention has been described in terms of specific items such as detailed elements as well as the limited embodiments and the drawings, they are only provided to help general understanding of the invention, and the present invention is not limited to the above embodiments. It will be appreciated by a person of ordinary skill in the art that various modifications and changes may be made from the above description.

Therefore, the spirit of the present invention shall not be limited to the embodiments described above, and the entire scope of the appended claims and their equivalents will fall within the scope and spirit of the invention.

What is claimed is:

1. A minimally invasive surgical instrument comprising:
a shaft through which a first wire and a second wire are conveyed;
an end effector connected to the shaft, wherein the end effector operates in a first rotational direction with respect to the shaft when the first wire operates in a first direction and the second wire operates in a second direction identical to the first direction, and the end effector operates in a second rotational direction with respect to the shaft when the first wire operates in a third direction and the second wire operates in a fourth direction opposite to the third direction;
an operating unit and a control unit to operate the end effector in the first rotational direction; and
at least one direction switch wire, which is connected and fixed to the operating unit and connects the operating unit and the control unit.

2. A minimally invasive surgical instrument as claimed in claim 1,
wherein the end effector comprises a roll gear, a first pinion, and a second pinion; and
the roll gear operates the end effector in the first rotational direction when the first pinion and the second pinion rotate in a same direction and the roll gear operates the end effector in the second rotational direction when the first pinion and the second pinion rotate in opposite directions.

3. A minimally invasive surgical instrument as claimed in claim 2,
wherein the first pinion and the second pinion are combined with a first pulley and a second pulley, respectively; and
the first pulley and the second pulley are wound with the first wire and the second wire, respectively.

4. A minimally invasive surgical instrument as claimed in claim 1, further comprising a first control unit comprising a third pulley wound with the first wire and a fourth pulley wound with the second wire,
wherein the end effector operates in the first rotational direction when the first control unit causes the third pulley and the fourth pulley to operate the first wire in the first direction and operate the second wire in the second direction.

5. A minimally invasive surgical instrument as claimed in claim 4, further comprising a handling unit, which comprises the first control unit and a second control unit and is connected to the shaft,
wherein the second control unit comprises a pair of upper rack gears connected with the first wire, a pair of lower rack gears connected with the second wire, an upper pinion geared between the pair of upper rack gears, a lower pinion geared between the pair of lower rack gears, and a roll control gear commonly geared to the upper pinion and the lower pinion, and
wherein the first control unit further comprises a main control unit connected and fixed to the shaft, and
wherein a part of the handling unit except the main control unit rotates together with the third pulley and the fourth pulley with respect to the main control unit.

6. A minimally invasive surgical instrument as claimed in claim 5, further comprising a fixing gear to fix a rotating state of the part of the handling unit except the main control unit, the third pulley, and the fourth pulley.

7. A minimally invasive surgical instrument as claimed in claim 4, further comprising an electric driving device to allow the third pulley and the fourth pulley to operate the first wire in the first direction and operate the second wire in the second direction.

8. A minimally invasive surgical instrument as claimed in claim 1, further comprising a second control unit, comprising:
a pair of upper rack gears connected with the first wire;
a pair of lower rack gears connected with the second wire;
an upper pinion geared between the pair of upper rack gears;
a lower pinion geared between the pair of lower rack gears; and
a roll control gear commonly geared to the upper pinion and the lower pinion.

9. A minimally invasive surgical instrument as claimed in claim 8, further comprising a roll sprocket to enable a user to rotate the roll control gear.

10. A minimally invasive surgical instrument as claimed in claim 8, further comprising an electric driving device to rotate the roll control gear.

11. A minimally invasive surgical instrument as claimed in claim 1, further comprising a handling unit connected to the shaft,
wherein the at least one direction switch wire is connected and fixed to the handling unit through the control unit.

12. A minimally invasive surgical instrument as claimed in claim 1, wherein the operating unit and the control unit comprise at least one fixed pulley, respectively; and
the at least one direction switch wire is hung around the at least one fixed pulley and pulled to switch the direction of the end effector.

13. A minimally invasive surgical instrument as claimed in claim 1,
wherein the at least one direction switch wires arc wire consists of two separate wires; and the two wires are to operate the end effector in the opposite directions to each other.

14. A minimally invasive surgical instrument as claimed in claim 1, further comprising a handling unit connected to the shaft, wherein the handling unit comprises an opening/closing handle connected with opening/closing wires to control the opening and closing of the end effector.

15. A minimally invasive surgical instrument as claimed in claim 14, wherein the handling unit further comprises a fixing handle to fix control states of the opening/closing handle, which may be grabbed together with the opening/closing handle.

16. A minimally invasive surgical instrument as claimed in claim 1, further comprising an electric driving device to push or pull the first wire and the second wire.

17. A minimally invasive surgical instrument as claimed in claim 1, wherein the first rotational direction is a yaw direction, and the second rotational direction is a roll direction.

18. A minimally invasive surgical instrument as claimed in claim 1, wherein the first rotational direction is a pitch direction, and the second rotational direction is a roll direction.

19. A minimally invasive surgical instrument comprising:
a shaft through which a first wire and a second wire are conveyed;
an end effector connected to the shaft, wherein the end effector rotates about a first axis in response to the first wire operating in a first direction and the second wire operating in a second direction identical to the first direction, and the end effector rotates about a second axis orthogonal to the first axis in response to the first wire operating in a third direction and the second wire operating in a fourth direction opposite to the third direction;
an operating unit and a control unit to rotate the end effector about the first axis; and
at least one direction switch wire, which is connected and fixed to the operating unit and connects the operating unit and the control unit.

* * * * *